(12) United States Patent
Sikora et al.

(10) Patent No.: US 7,323,180 B2
(45) Date of Patent: Jan. 29, 2008

(54) USE OF CROSS-PROTECTION TO IDENTIFY NOVEL VACCINE CANDIDATES FOR INFECTIOUS AGENTS

(75) Inventors: Christopher Sikora, Manitoba (CA); Bradley Berger, Alberta (CA); John Cherwonogrodzky, Alberta (CA)

(73) Assignee: Her Majesty The Queen in right of Canada represented by the Minister of National Defence of Her Majesty's Canadian Government, Ottawa, Ontario (CA)

( * ) Notice: Subject to any disclaimer, the term of this patent is extended or adjusted under 35 U.S.C. 154(b) by 463 days.

(21) Appl. No.: 10/762,241

(22) Filed: Jan. 23, 2004

(65) Prior Publication Data

US 2004/0151736 A1    Aug. 5, 2004

Related U.S. Application Data

(60) Provisional application No. 60/442,072, filed on Jan. 24, 2003.

(51) Int. Cl.
*A61K 39/02* (2006.01)

(52) U.S. Cl. ............................ 424/234.1; 424/236.1; 530/350

(58) Field of Classification Search ............ 424/234.1, 424/236.1; 530/350
See application file for complete search history.

(56) References Cited

OTHER PUBLICATIONS

Stewart, *Francisella*, Chapter 43, Manual of Clinical Microbiology, Fifth Edition, pp. 454-456.
Franz et al, Clinical Recognition and Management of Patients Exposed to Biological Warfare Agents, JAM, Aug. 6, 1997, vol. 278, No. 5, pp. 399-411.
Evans et al, Tularemia, Chapter 24, Medical Aspects of Chemical and Biological Warfare, pp. 504-512.
Cherwonogrodzky et al, Increased encapsulation and virulence of *Francisella tularensis* live vaccine strain (LVS) by subculturing on synthetic medium, Vaccine 1994, vol. 12, No. 9, pp. 773-775.
Corbel, Recent Advances in the Study of Brucella Antigens and their Serological Cross-Reactions, Veterinary Bulletin, Commonwealth Agricultural Bureaux, Dec. 1985, vol. 55, No. 12, pp. 927-942.
Abstracts, 4. Medizinische B-Schutz-Tagung des BMVg, am 22. und 23. Oktober 1997.
Golovliov et al, Adjuvanticity of ISCOMs incorporating a T cell-reactive lipoprotein of the facultative intracellular pathogen *Francisella tularensis*, Vaccine, 1995, vol. 13, No. 3, pp. 251-267.
Hood, Virulence factors of *Francisella tularensis*, Journal of Hygiene, 1977, vol. 79, No. 1, pp. 47-60 (with 5 plates).
Ancuta et al, Inability of the *Francisella tularensis* Lipopolysaccharide to Mimic or to Antagonize the Induction of Cell Activation by Endotoxins, Inspection and Immunity, Jun. 1996, vol. 64, No. 6, pp. 2041-2046.
Conlan et al, Mice vaccinated with the O-antigen of *Francisella tularensis* LVS lipopolysaccharide conjugated to bovine serum albumin develop varying degrees of protective immunity against systemic or aerosol challenge with virulent type A and type B strains of the pathogen, Vaccine 20 (2002), pp. 3465-3471.
Cherwonogrodzky, Factors Controlling Haemolysin Production in *Vibrio Parahaemolyticus*, 1983, pp. 161-162.

*Primary Examiner*—Jennifer E. Graser
(74) *Attorney, Agent, or Firm*—Nixon & Vanderhye P.C.

(57) ABSTRACT

This invention discloses methods for identifying *Francisella tularensis* vaccine candidates. It enables identification of novel vaccine candidates and quality assurance for vaccine batches, assessment of protection in vaccinates and identification of the infecting agent in vaccinates. Mice were first vaccinated with *Brucella abortus* O-polysaccharide (OPS) vaccine. These animals were then given 10 $LD_{50}$s of *F. tularensis* live vaccine strain (LVS). Sixty percent (60%) of the vaccinated mice survived the multiple lethal doses. Sera were collected from these surviving mice and the antibodies were used to probe supernatant and cell lysates of live *F. tularensis* LVS cultures. Several *F. tularensis* components were identified only by the noted "survivor" antisera. Of these identified proteins, enzyme digestions and chemical oxidation suggest post-translational modifications of some proteins e.g. a 52 kDa glycoprotein, a 45 kDa lipoprotein and a 19 kDa nucleoprotein. The 52 kDa component caused nitrous oxide induction in tissue cultures at low concentrations, cell death at high concentrations. Vaccination with this gave partial protection while addition of other components acted synergistically to give enhanced protection from 250 $LD_{50}$s of *F. tularensis* LVS.

2 Claims, 9 Drawing Sheets

USE OF CROSS-PROTECTION TO IDENTIFY NOVEL VACCINE CANDIDATES FOR INFECTIOUS AGENTS

CROSS REFERENCE TO RELATED APPLICATION

This application claims the benefit of Provisional Application No. 60/442,072, filed Jan. 24, 2003, the entire content of which is hereby incorporated by reference in this application.

FIELD OF THE INVENTION

The general field of the invention is the development of sub-cellular vaccines that induce immunity to infectious agents. More particularly, the invention relates to the identification of novel vaccine candidates (with logical extensions to other infectious agents such as other bacteria, fungi, yeast, viruses or parasites), quality assurance for vaccine batches, assessment of protection in vaccinated animals and the identification of the infecting agent in vaccinates.

BACKGROUND OF THE INVENTION

List of Prior Art Literature
Stewart, S. J. 1991. *Francisella*. In: Balows, A., W. J. Hausler, Jr., K. L. Herrmann, H. D. Isenberg, and H. J. Shadomy (ed.). Manual of Clinical Microbiology. Am. Society for Microbiology, pp. 454-456.
Franz, D. R., P. B. Jahrling, A. M. Friedlander, D. J. McClain, D. L. Hoover, W. R. Bryne, J. A. Pavlin, G. W. Christopher and E. M. Eitzen, Jr. 1997. Clinical recognition and management of patients exposed to biological warfare agents. JAMA, 278:399-411.
Evans, M. E., and A. M. Friedlander. Tularemia. In: F. R. Sidell, E. T. Takafuji and D. R. Franz (ed.) Medical Aspects of Chemical and Biological Warfare. 1997. Published by the Office of the Surgeon General at TMM Publications. pp. 503-512.
Cherwonogrodzky, J. W., M. H. Knodel, and M. R. Spence. 1994. Increased encapsulation and virulence of *Francisella tularensis* live vaccine strain (LVS) by subculturing on synthetic medium. Vaccine. 2:773-775.
Corbel, M. J. Recent advances in the study of *Brucella* antigens and their serological cross-reactions. 1985. Veterinary Bulletin. 55: 927-942.
Sjostedt, A. 1997. Host-parasite interactions during tularemia. (Introductory remarks to the presentation, given at the Medical Protection B Conference, Munich, Germany).
Golovliov, I., M. Ericsson, L. Akerblom, G. Sandstrom, A. Tarnvik and A. Sjostedt. 1995. Adjuvanicity of ISCOMS incorporating a T-cell reactive lipoprotein of the facultative intracellular pathogen *Francisella tularensis*. Vaccine. 13:261-267.
Hood, A. M. 1977. Virulence factors of *Francisella tularensis*. J. Hyg. Camb. 79: 47-60
Ancuta, P., T. Pedron, R. Girard, G. Sandstrom and R. Chaby. 1996. Inability of the *Francisella tularensis* lipopolysaccharide to mimic or to antagonize the induction of cell activation by endotoxins. Infect. Immun. 64: 2041-2046.
Conlan, J. W., H. Shen, A. Webb, M. B. Perry. 2002. Mice vaccinated with the O-antigen of *Francisella tularensis* LVS lipopolysaccharide conjugated to bovine serum albumin develop varying degrees of protective immunity against systemic or aerosol challenge with virulent type A and type B strains of the pathogen. Vaccine 20: 3465-3471.
Cherwonogrodzky, J. W. 1983. Factors controlling haemolysin production in *Vibrio parahaemolyticus*. Ph.D. thesis, University of Toronto, pages 161-162.

Tularemia is primarily a disease of wildlife that spreads to humans incidentally such as by insect or tick bites, handling infected carcasses or by drinking contaminated water. The disease usually progresses from an ulcer (at the site of infection or within the bowel if ingested) to oculoglandular infections (eyes are stressed and 'flu'-like symptoms such as chills, fever, headache and general aches and pains becoming progressively worse) then systemic gastrointestinal or pleuropneumonia tularemia that causes severe illness with a high mortality rate (30-60%) unless antibiotic therapy is given. Although the incidence of tularemia has declined with the decline of market hunting and trapping, it is still widespread around the globe, infecting wildlife, domestic animals and humans (Stewart, 1991). The bacterium is readily grown on simple medium with a cysteine supplement, and it is highly virulent when delivered as an aerosol or in contaminated water. It is a potential threat agent for biological warfare or terrorist programs (Franz et al., 1997).

With regards to medical countermeasures against tularemia, antibiotics can clear the infection, but the success of these antibiotics depends on where the infection has located and how early the patient is treated. A *F. tularensis* live vaccine strain (LVS) is available, but it has an IND (Investigational New Drug) status, its efficacy against exposures by different routes of infection is questionable (Evans and Friedlander, 1997) and under certain conditions it appears to revert to its virulent parental form (Cherwonogrodzky et al., 1994). There is therefore a need for both a new, more effective and safe vaccine, a means of assessing the stability of different batches of the existing LVS vaccine, and for assessing by a simple blood test if a vaccinate is indeed protected from tularemia. As *Brucella* and *F. tularensis* cross-react (Corbel, 1985), it would benefit serodiagnosis if an antigen could determine which bacterium had infected a patient.

In theory, it might be viewed that sera from either vaccinated or infected animals or humans might have antibodies that could identify components key to the disease process and hence potentially useful as vaccine candidates. To date this has not happened. For the first part, vaccination often gives limited results (e.g. although the LVS protects against tularemia, its efficacy for protecting against infection by different routes is questionable) with antibody titers either being low or rapidly diminishing with time. For the second part, infected animals or human have an illness where the immunity has either failed or has responded incorrectly to what was required for protection. Indeed, Edward Francis (from whom Francisella is named) had 3 infections of tularemia and eventually died from this disease (Sjostedt, 1997). An infection did not provide Francis with immunity. Although sera from vaccinated or infected patients do have antibodies with affinity for low molecular proteins of *F. tularensis*, these proteins do not appear to give protection when used as vaccines (Golovliov et al., 1995). The approaches used by the experts in the field to date teach away from novel approach of the present invention on how to identify potentially useful components.

In a previous publication (Cherwonogrodzky et al., 1994), the capsule of *F. tularensis* was viewed as a virulence factor. However, in subsequent studies it was found that this was not the case. Mice did not become ill when they were infected with *F. tularensis* live vaccine strain subcultured more than 6 times in a synthetic salts medium, even though these bacteria still had extensive capsules. Evidently the initial speculation on the role of capsules for virulence of the bacterium was incorrect and teaches away from the later findings.

With regards to toxins, the current state of knowledge is that toxins are not present for *F. tularensis* (Hood, 1977; Ancuta et al., 1996). In unpublished studies, we found that when the third (broth or agar) subculture had the supernatant filter-sterilized (0.2 μm filter used), and 0.05 ml was given to mice intranasally, initially the mice appeared normal. This initial observation appeared to confirm the existing state of knowledge that no toxins were present in *F. tularensis* cultures. However, 24 hours after the supernatant inoculation, all mice were found dead in their cages. These latter (unreported) results proved, contrary to the literature, that a toxic agent was being produced by the bacterium but that it had a delayed action on the test animals.

SUMMARY OF THE INVENTION

It is an object of the present invention to provide a safe and effective vaccine against tularemia. The methods disclosed will be applicable to other infectious diseases such as those caused by other bacteria, fungi, yeasts, viruses and parasites.

A mouse model is used which can be extended to any mammal. Mice are vaccinated with a polysaccharide from one bacterium (i.e. *Brucella*) so as to survive multiple lethal doses of another cross-reactive bacterium (*F. tularensis*). The "survivor" serum is used as a source of unique antibodies to identify virulence factors of the latter bacterium.

Specifically, mice were given a vaccine against one bacterium (O-polysaccharide, or OPS vaccine which is protective against *Brucella abortus*) but then infected with multiple lethal doses (10 $LD_{50}$) of another bacterium, *Francisella tularensis*. Due to cross-protection, most of the mice vaccinated against brucellosis survived tularemia. It was found that these surviving vaccinated mice had in their sera antibodies that recognized the latter bacterial components expressed during the disease process. That these mice had sera with antibodies that recognized previously overlooked proteins showed a novel method for finding vaccine candidates and for assessing protection. That some of these components were specific to *Francisella tularensis* provided a means of differentiating the infecting agent, even in the presence of cross-reactions that currently confuse identification.

A further object of the present invention is to demonstrate the expression of toxic components in culture supernatants that could be identified and quantified with the novel antibodies. An application for the assessment of these components is a quality assurance measure for different vaccine lots of *F. tularensis* live vaccine strain.

According to one aspect of the invention, it provides a subcellular protein expressed from *Francisella tularensis* infected mammal subculture growing in synthetic salts medium of weak acidity.

According to another aspect of the invention, it provides a method for identifying an infectious agent in a mammal, comprising vaccinating the mammal against a first infectious agent and subsequently exposing the mammal to a second infectious agent to be identified, thereby causing the mammal to express a subcellular protein against the second infectious agent.

The far right lane is the Rainbow™ Marker (M) which has standard proteins of different molecular weights.

Figure 2:
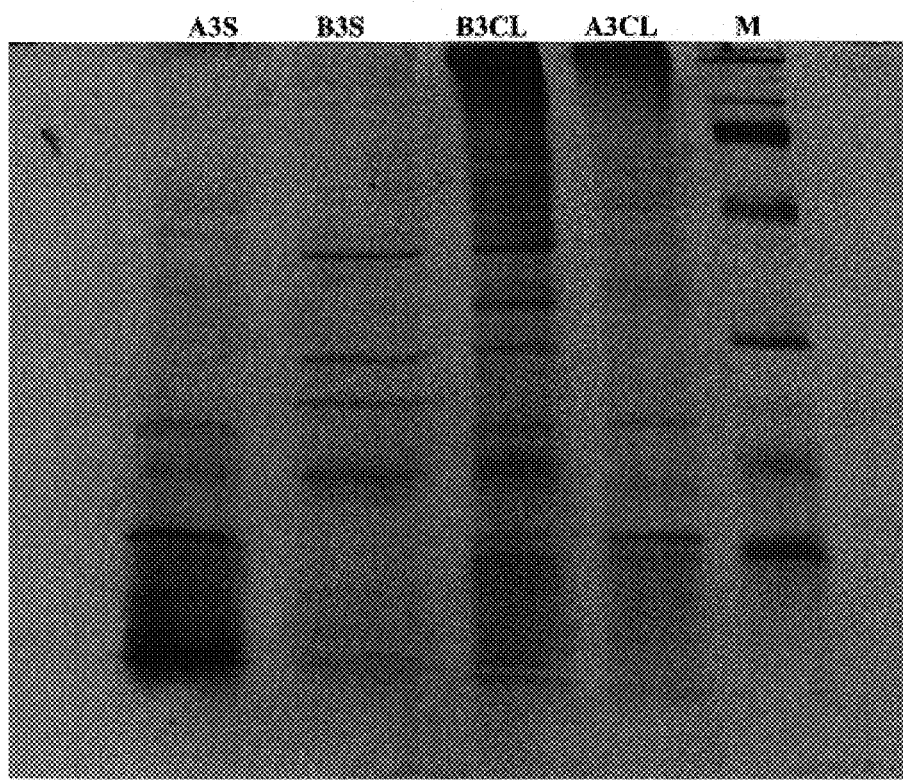

FIG. 2 shows a 12% SDS PAGE, Silver Stain, of *Francisella tularensis* live vaccine strain (LVS) subcultured on synthetic salts medium (Chamberlain's).

Lane A3S shows proteins released into the agar of agar subculture #1, B3S are the proteins released into the supernatant of broth subculture #3. Lane B3CL are the proteins from the cell lysate of broth subculture #3, A3CL are the proteins from the cell lysate of agar subculture #3. Lane M is the Rainbow™ molecular weight markers.

Figure 3:
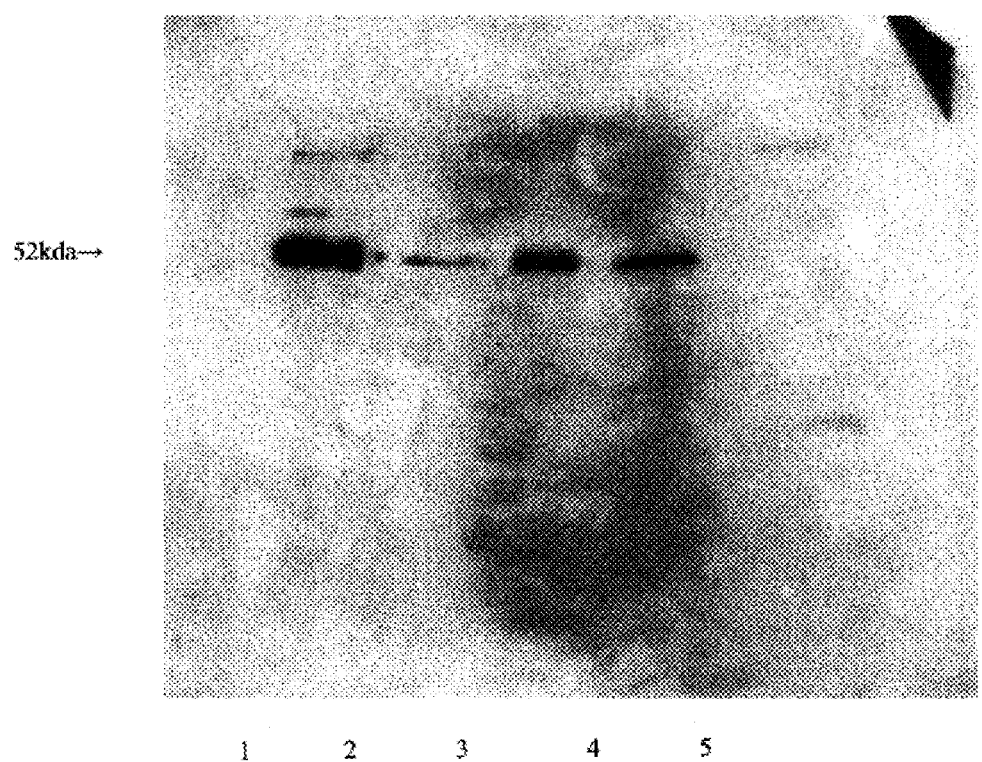

FIG. 3 shows an immunoblot (Western) of *F. tularensis* cellular components.

Samples electrophoresed on an 12% SDS PAGE with 0.75 mm thickness and transblotted as described. Primary antibody: 1:50 *Brucella*-OPS primed anti *F. tularensis* murine antisera. Secondary antibody: 1:3000 Caltag anti-mouse-HRP Lane 1: broth subculture 1, lane 2: broth subculture 2, lane 3: broth subculture 4, lane 4: broth subculture 5, lane 5: 5 μL Rainbow MW marker.

Figure 4:
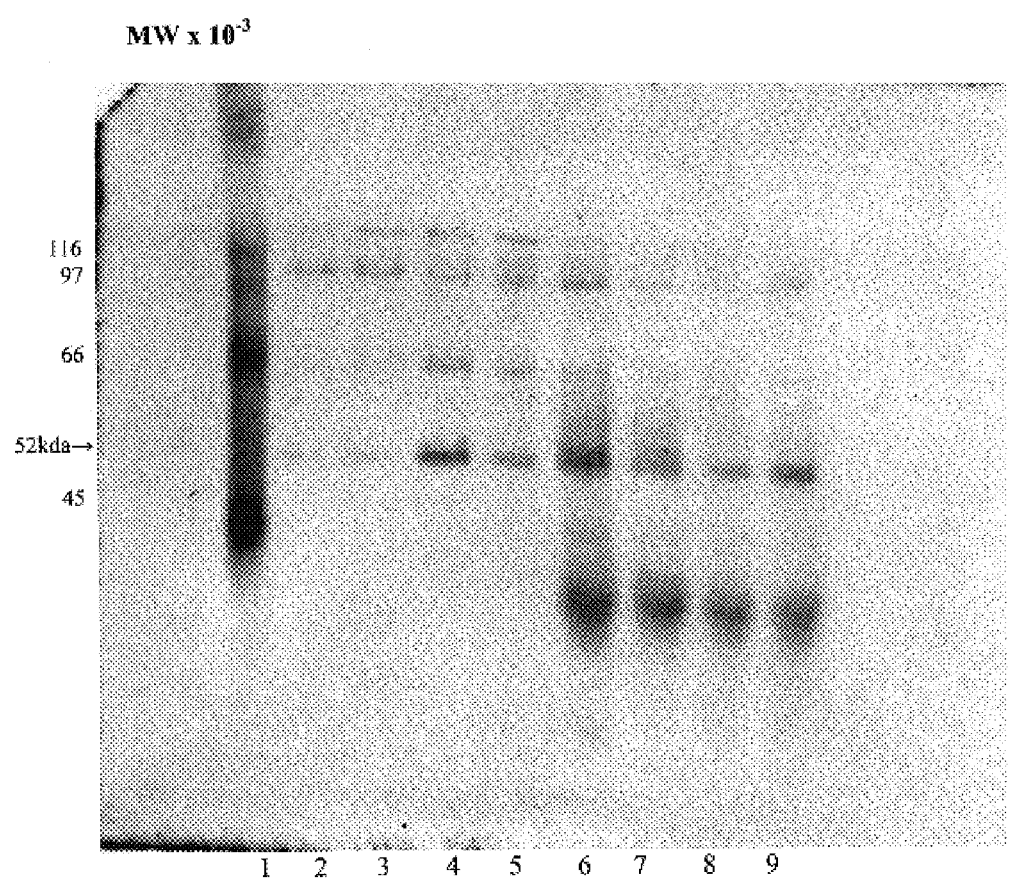

FIG. 4 shows an immunoblot (Western) Characterization of *F. tularensis* LVS cellular components.

Samples preparred and electrophoresed under normal polarity on a 7.5% native (no SDS) gel of 1.0 mm thickness as described. Primary antibody: 1:50 *Brucella*-OPS primed anti *F. tularensis* murine antisera. Secondary antibody: 1:3000 Caltag anti-mouse-HRP Lane 1: BioRad H/L MW marker (5 μL), Lane 2: 24 hr growth, Lane 3: 48 hr growth, Lane 4: 72 hr growth, Lane 5: 96 hr growth, Lane 6: 5 day growth, Lane 7: 6 day growth, Lane 8: 7 day growth, Lane 9: 8 day growth.

Figure 5:
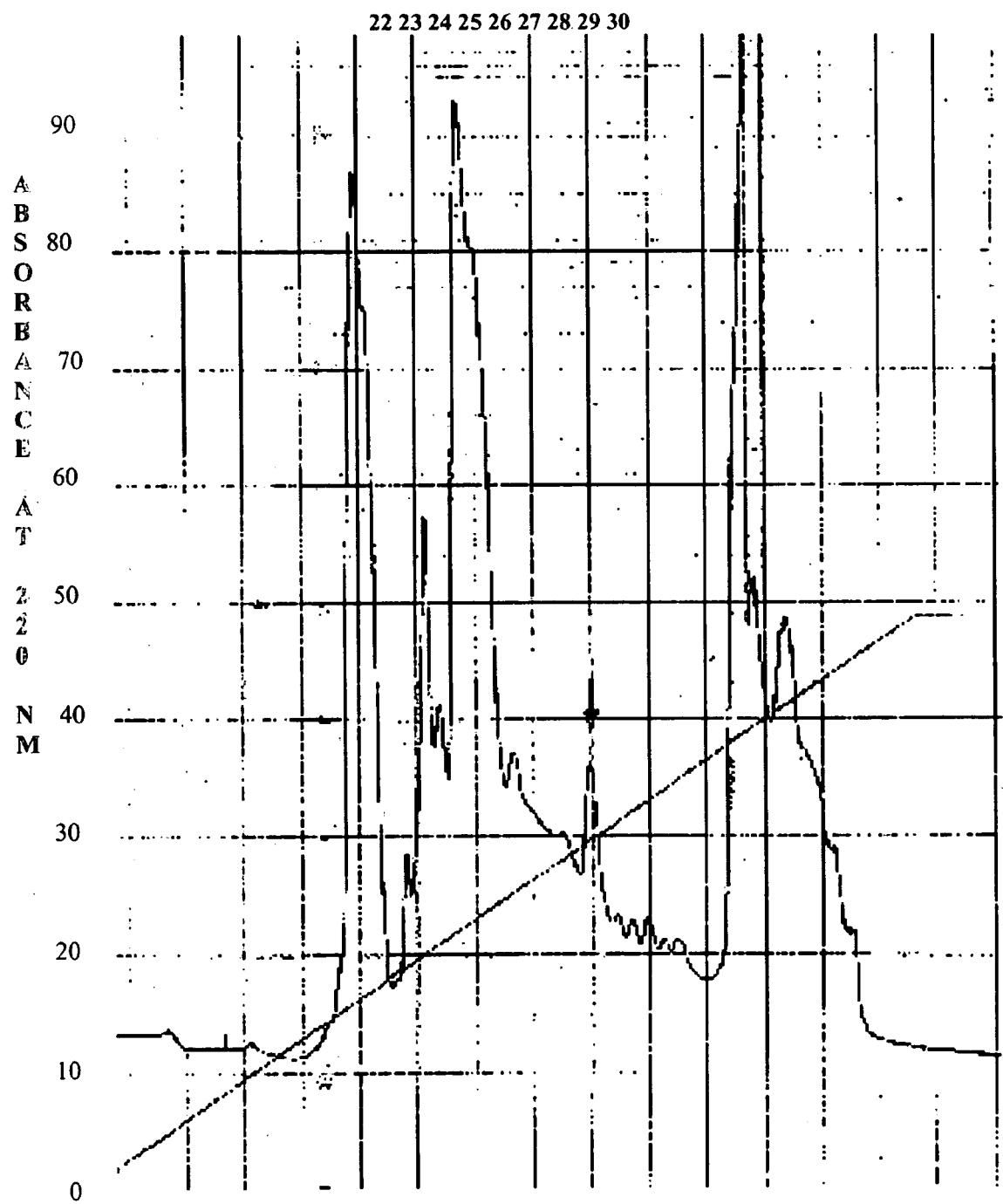

FIG. 5 shows an elution profile (absorbance at 220 nm) of proteins eluted from a Pharmacia Mono-Q™ column.

Source of material was *F. tularensis* LVS lysate (cell disrupted by sonication) that was partially purified with an Amicon Filtration device (molecular weight cutoff of 30 kDa)

Figure 6:
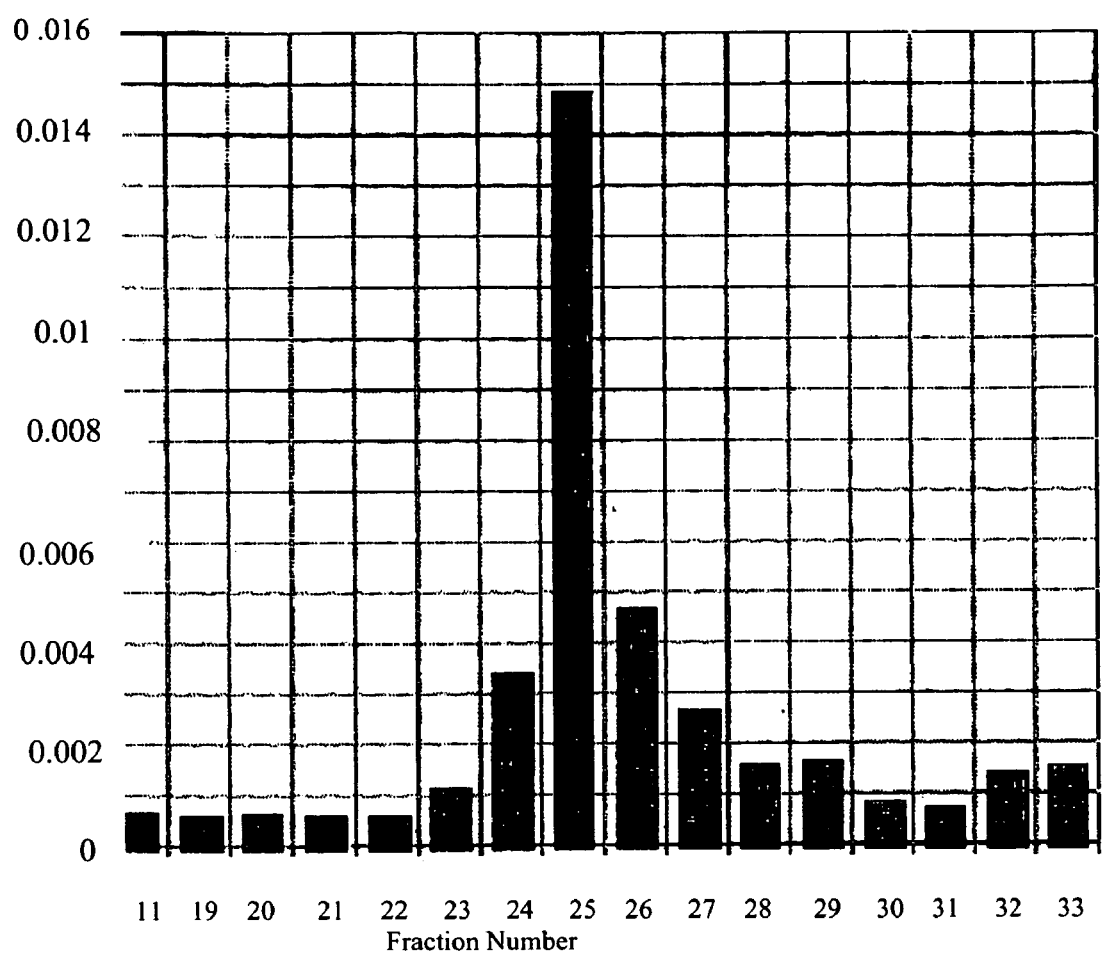

FIG. 6 indicates Nitric Oxide (NO) production by J774.1 macrophage cells in response to treatment by Mono-Q separated fractions of *F. tularensis* LVS cell lysate for 24 hr.

Figure 7:
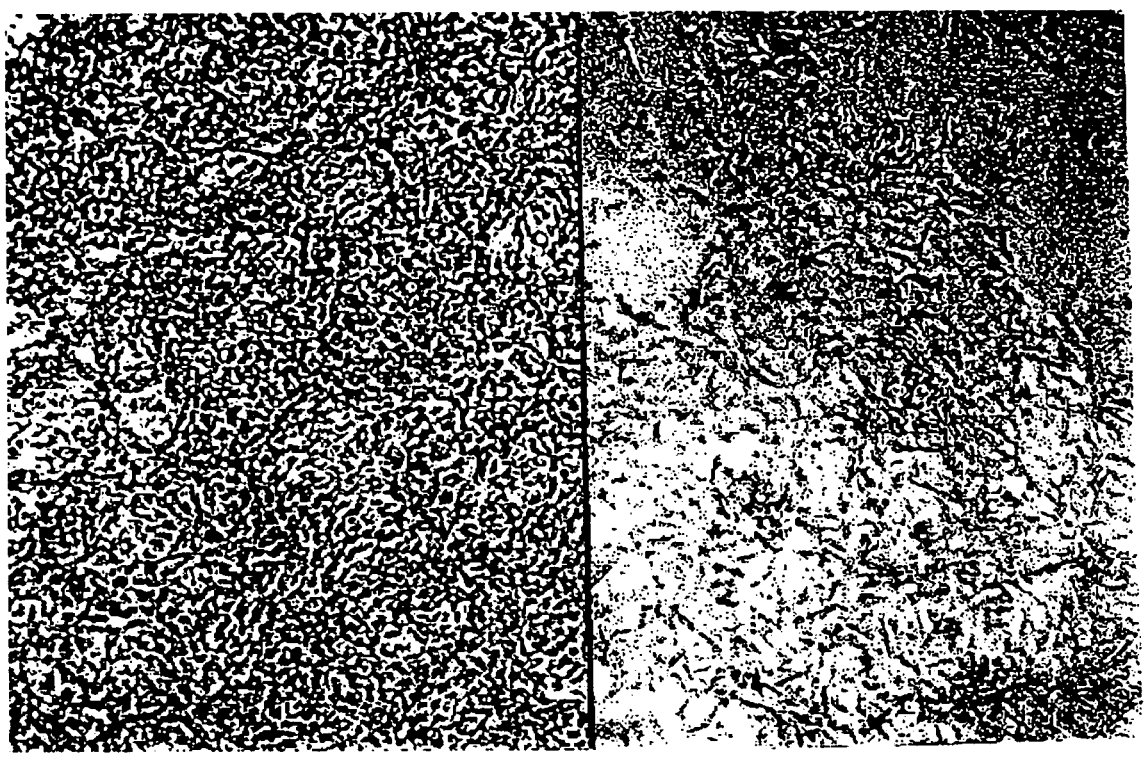

FIG. 7 shows Vero tissue cultures.

Photograph on the left is the control; photograph on the right is cell death as a result of the addition of 3 mg/ml of the *F. tularensis* LVS 52 kDa protein.

Figure 8:
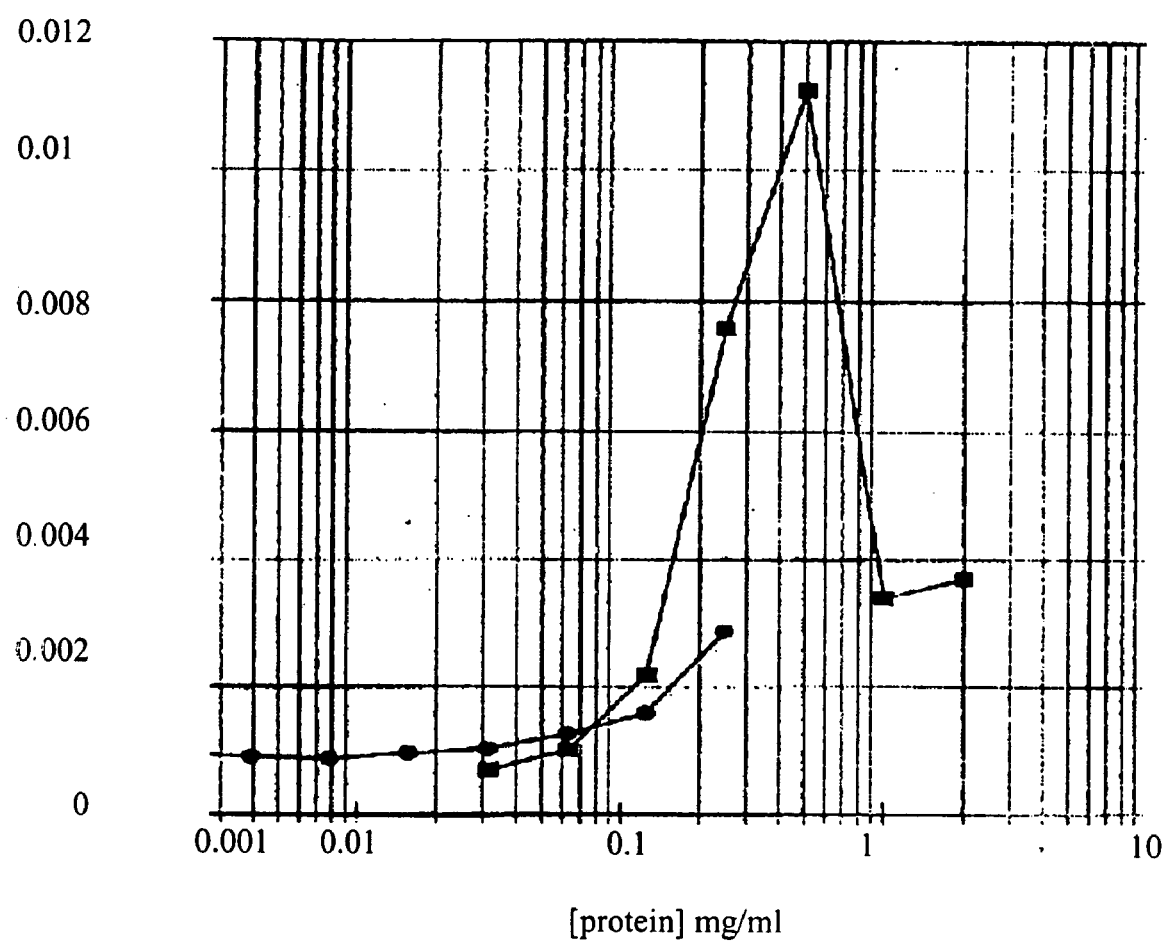

FIG. 8 shows Nitrous oxide (NO) production of Vero tissue cultures when given increasing amounts of the *F. tularensis* 52 kDa protein.

Figure 9:
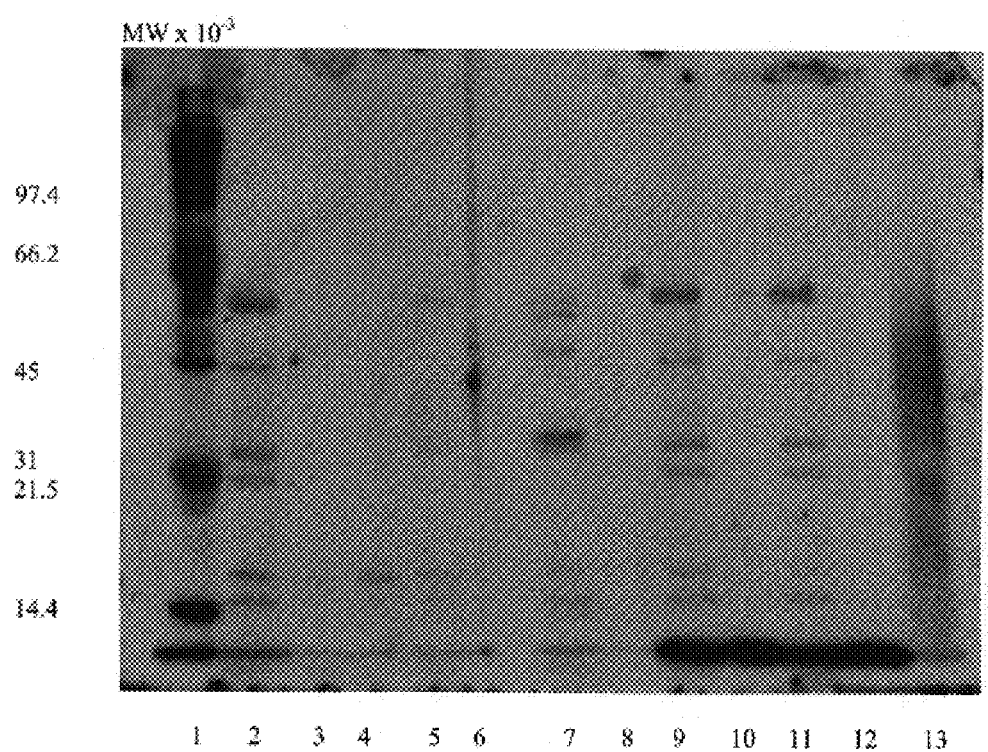

FIG. 9 shows enzyme characterization and immunoblot (Western) of antigenic *F. tularensis* liquid culture cellular components.

Supernatant from Day7 of the multiday growth series used (7D). Supernatant concentrate (1.88 μg) was treated with various enzymes (0.83 μg). Samples prepared and electrophoresed on a 7.5% SDS-PAGE of 1.0 mm thickness as described and transblotted onto nitrocellulose. Membrane probed under the following conditions: Primary antibody: 1:1000 *Brucella*-OPS primed anti *F. tularensis* murine antisera. Secondary antibody: 1:3000 Caltag anti-mouse-HRP Lane 1: BioRad H/L MW marker (5 μL), Lane 2: 7D supernatant, Lane 3: Proteinase-K digested supernatant, Lane 4: Proteinase-K, Lane 5: Lipase digested supernatant, Lane 6: Lipase, Lane 7: DNAse digested supernatant, Lane 8: DNAse, Lane 9: RNAse digested supernatant, Lane 10: RNAse, Lane 11: Lysozyme digested supernatant, Lane 12: Lysozyme, Lane 13: BioRad Kailadoscope MW marker (6 µL).

DETAILED DESCRIPTION OF THE INVENTION

Our laboratory has taken an approach (i.e. identifying useful subcellular components) contrary to the existing scientific methods (i.e. forming live attenuated mutants) on tularemia vaccine development. Our successes were based on our past unreported observations:

(a) We have discovered that subculturing *F. tularensis* LVS in a synthetic medium stresses the bacterium and causes enhanced expression of a capsule. For other infectious bacteria (e.g. those that cause whooping cough and pneumonia), the presence of a capsule is indicative of the pathogenicity of the bacterium and severity of illness in the host. This teaches away from our later observation that, after a few subcultures in the synthetic medium, bacteria continued to be capsulated but were non-lethal for the mice tested. Thus, lethality is due to a factor or factors other than the capsule.

(b) Toxins usually act immediately on host target cells because of their detergent (e.g. bee venom toxin) or enzymatic (e.g. diphtheria toxin) activity. The existing state of knowledge in the scientific community is that *F. tularensis* does not produce toxins. Our own work initially supported this accepted dogma. When *F. tularensis* LVS was grown in synthetic media, cells removed by centrifugation and then the culture supernatant filter-sterilization (0.2 um filtration), no effects were observed when 50 µl of this supernatant was inoculated into the nostrils of anaesthetized mice. However on the second day, all inoculated mice were found dead in their cages. There was an unobvious toxin or toxins from *F. tularensis* that we almost missed because these caused delayed death.

(c) In one study, *F. tularensis* LVS was reverted to a more pathogenic state by subculturing in synthetic medium. Ten LD50s were administered to several mice by different routes (intra-nasally, intra-peritoneally, intravenously). Past results showed that mice died in 5-8 days when given this dose and so on the fifth day mice were sacrificed to understand the disease process leading to death. Curiously, despite the different routes of administration of the bacterium and the presence of the bacterium in the blood and organs, histology revealed that only the lung was affected. For tularemia, it was observed that microscopic foci of necrosis and pneumonia occurred in the lungs of mice. The lack of significant histology with the other tissues may give evidence why the effects of a toxin have not been observed by other research laboratories. Although we found that a toxin was produced, the action was unobvious, affecting only susceptible tissue (lung) in susceptible animals (mice). Had other tissues from other animals been investigated, it is likely we would have also missed this effect.

The usual method to identify a bacterial component is to vaccinate an animal with the killed bacteria, take the serum and probe with antibody in these components on acrylamide gels. Using commercial rabbit antiserum (rabbits that had been vaccinated with killed *F. tularensis* cells) did not reveal anything different from other reported studies.

It is known that *Brucella abortus* cross-reacts with *F. tularensis*. Mice were infected with live *B. abortus* (i.e. by using live untreated cells that would grow inside the host, it was hoped that key antigens would be intact for an antibody response), their serum collected, filter-sterilized and sterility-checked. However, this antiserum did not reveal anything different or striking when used to tag *F. tularensis* cell components separated on acrylamide gels.

Despite the above negative results that would have led anyone skilled in the art to conclude that nothing different or striking was being expressed by the reverted *F. tularensis*, we believed otherwise. Our unpublished results noted above showed that something toxic was being expressed but that standard methods for detection were inadequate. To resolve this impasse, innovative methods were developed and used that are described below.

Other investigators have used, as vaccines, killed or attenuated (weakened by genetically manipulation) microbial agents that do not express components critical to the disease process. Highly virulent agents are not used because the end result is a dead animal. Our invention used a vaccine to one bacterium (the O-polysaccharide from *Brucella abortus*) to protect mice against several lethal doses (10 $LD_{50}$s) of another bacterium, *Francisella tularensis*, by cross-protection. All mice initially did show preliminary symptoms of infection. About 60% of the vaccinated animals rapidly recovered from the multiple lethal doses. These mice had antibodies that identified previously unknown agent components. These components were not identified with serum taken from mice infected with *B. abortus* or vaccinated with killed *F. tularensis* cells. Some of these components were characterized, purified and used as vaccines. These were also used to assess the quality assurance for different vaccine (*F. tularensis* LVS) subcultures.

A recent publication (Conlan et al., 2002) teaches away from both the usefulness of *B. abortus* OPS vaccine to protect against tularemia, and to protect against a respiratory (i.e. intranasal) challenge of tularemia. For the former, the compositions of OPS from *B. abortus* and that of *F. tularensis* are dissimilar. Whereas the OPS of *B. abortus* is a 1,2 linked formamido-mannose polymer, the OPS of *F. tularensis* has different sugars and linkages. In addition, although the latter had some efficacy in protecting mice from intradermal challenges of *F. tularensis*, these "were completely unprotected against a low dose aerosol challenge with this strain". In contrast, we did find that the *B. abortus* OPS vaccine protected mice from tularemia and from a respiratory challenge.

Another unobvious, and also unfortunate, observation was the effect of freeze-thaw on the special ("survivor") serum. This caused the antibodies to bind to *F. tularensis* cell lysate proteins in a different binding profile. Results were similar to published information in the literature whereby antibodies bound to a greater extent to low molecular weight components (shown by others to be of no use as vaccine candidates) and far less to the larger molecular weight components. As frozen-and-thawed sera from control unvaccinated mice gave similar results, it is likely that the freeze-thaw caused denaturation and hence non-specific binding of the antibodies. Much of the work presented in this patent, therefore, is based on identification of vaccine components by using fresh unfrozen serum, stored in the refrigerator at 4° C. when not in use.

MATERIALS AND METHODS

Bacterial Cultures

*Francisella tularensis* live vaccine strain (LVS) was acquired as a freeze-dried vaccine in a vial (Lot #11, Code Number: NDBR 101, 2.4×10$^9$ cfu/ml when rehydrated) from the United States Army Medical Research Institute of Infectious Diseases (USAMRIID), Frederick, Md., USA. It was grown either on agar or in broth synthetic medium at 37° C., 90% humidity and 5% $CO_2$. For intranasal inoculation, 10 $LD_{50}$ was 1×10$^5$ bacteria diluted in 37° C. prewarmed phosphate buffered saline (PBS). These bacteria were in 0.01 ml PBS given intranasally by Eppendorf™ pipette tip to anaesthetized Balb/c mice. For intraperitoneal injections, 10 $LD_{50}$ was 1×10$^6$ bacteria in 0.1 ml PBS.

*Brucella abortus* strain 30 was acquired from the Animal Diseases Research Insitute-Nepean, (ADRI-Nepean), Ontario. This was maintained on *Brucella* agar with 1.5 ppm crystal violet and incubated as for LVS. This culture was used to infect mice (within our Biocontainment Level 3 facilities) for sera against live *Brucella abortus*.

Five-percent phenol-killed *B. abortus* 1119-3 was acquired from Dr. Janet Payeur, United States Department of Agriculture (USDA), Ames, Iowa. These cells were used as the source for O-polysaccharide vaccine which was purified by a method previously described (Cherwonogrodzky et al., 1990).

To compare antigen expression of LVS to other bacteria, 4 bacteria were used. *Staphylococcus aureus* ATCC 25923 (as an antibody-binding positive control) was from Fisher Scientific (Ottawa, Bactrol Discs Set A). *Escherichia coli* O:157, H:7, *Salmonella godesburg* and *Pseudomonas maltophilia* 555 (which all have OPS that cross-react with *Brucella*) were obtained from Dr. Douglas Griffith (NRC, Ottawa).

Bacterial Growth Media

For *F. tularensis* LVS, the synthetic medium base consisted of 1% NaCl, 0.4% glucose, 0.1% (each)/$KH_2PO_4$ and $K_2HPO_4$, 0.2% (each) L-proline and DL-threonine, 0.04% (each) of L-arginine, L-asparagine, DL-isoleucine, L-leucine, L-lysine HCl, DL-methionine, DL-serine, L-tyrosine and DL-valine, 0.02% (each) L-cystine HCl and L-histidine, 0.0135% $MgSO_4 \cdot 7H_2O$, 0.40 parts per million (ppm) spermine phosphate, 4 ppm thiamine HCl, 2 ppm DL-calcium pantothenate and $FeSO_4 \cdot 7H_2O$ (in triply distilled water, filter sterilized, pH 6.5). For broth cultures, a vial of stock culture was taken from the −70° C. freezer, partially thawed and a loopful was used to inoculate 10 ml peptone-cysteine broth tubes. These were incubated for a few days until growth was obvious. These were then added to 500 ml synthetic medium base in 1 litre sterile flasks then incubated for early logarithmic or late stationary phases (shaken at 150 rpm, 37° C.). For agar plates, a double strength of the synthetic medium was made and placed in a 50° C. water bath, a 4% agar (Difco Laboratories, Detroit, Mich.) in distilled water suspension was autoclaved (30 min, 121° C., 15 psi), cooled to 50° C., then these were combined and used to make pour plates.

For *Brucella abortus* 30, this was maintained on *Brucella* agar with 1.5 ppm crystal violet, subcultured in *Brucella* broths (without crystal violet) at 37° C., 5% $CO_2$ and 150 rpm.

For the 4 other bacteria noted, these were grown in Luria Broth (Difco Laboratories, Detroit, Mich.; 10 g/L Bacto-peptone, 5.0 g/L Bacto yeast extract and 10 g/L sodium chloride), then incubated, centrifuged and sonicated as noted for LVS in this section.

Sonication

For sonicating particulate suspensions, a Soniprep 15™ and a Process Timer™ (both manufactured by MSE™) were used. Samples were in plastic tubes which were held with a clamp and partially immersed in ice-water in a small beaker. The amplitude of the 10 mm probe was adjusted manually to 10 µm, the sequence was 5 cycles of 15 second pulses followed by 1 min chilling. For the sonication of a live culture of *F. tularensis* LVS, two 500 ml cultures were centrifuged (10,000×g, 4° C., 30 min), the white pellet was resuspended in 75 ml of sterile PBS then stored frozen at −70° C. Prior to use, this was thawed at room temperature (22° C.). Sonication on these freeze-thawed stressed cells was as before except that 10 ml aliquots were used and 12 cycles were used for a total homogenization time of 3 minutes. (Due to BL-2 aerosol hazards, the entire sonicator was placed inside a BioSafety Cabinet and decontaminated with 70% ethanol from a spray bottle prior to removal.) The disrupted cell suspension was centrifuged (10,000×G, 30 min) then the supernatant of the cell lysate was saved.

Use of Animals (Mice)

Mice (usually balb/c, female, 19-21 g, 35 days old) were acquired from Charles River (St. Constant, Quebec). Mice were cared for in accordance with the guidelines set by the Canadian Council for Animal Care. All procedures were reviewed and approved by the DRDC Suffield Animal Care Committee (members consist of a veterinarian, scientists and lay people from the community). Protocol JC-98-02 was used for this study. To raise anti-tularemia mouse sera, twenty mice were first vaccinated with the *B. abortus* OPS. Each mouse was given 1 µg OPS in 0.1 ml sterile saline by the intraperitoneal route (i.p.). Two weeks later, these mice were taken to a BioSafety Cabinet, infected with 10 $LD_{50}$ of *F. tularensis* LVS (only BL-2 containment is required) which was diluted in sterile prewarmed PBS and given i.p. Infected mice were then placed into isolator cages (with adequate food and water, with HEPA filter tops) which in turn were placed into a HEPA-filtered Animal Isolator (Thoren Caging, Toronto). The mice were monitored for 2 weeks. About 60% of the OPS vaccinated mice survived 10 $LD_{50}$ of *F. tularensis* LVS and then these were sacrificed for their anti-tularemia serum. For infection by the intranasal route, mice were anaesthetized with 0.1 ml of 1:10 diluted Somnitol™ given intraperitoneal (as anaesthetized mice are sensitive to the cold, it is imperative that their surrounding temperature be about 22° C., also a heat lamp at a distance may be needed to assist their recovery) then 0.01 ml of the bacterial suspension was delivered to a nostril by an Eppendorf™ tip.

Sera

Blood was collected into 1.5 ml small Eppendorf™ centrifuge tubes. Small volumes (0.1-0.3 ml) were collected by inserting a 26-gauge needle into a warmed tail vein (i.e. warmed with a heatlamp), then with an Eppendorf™ tip transferring the blood from the needle cap to the centrifuge tube. Larger volumes (1 ml) were collected by first anaesthetizing mice with a double dose of Somnitol™, then doing a heart-puncture with a 1 ml syringe with a 26-gauge needle attached. The blood was centrifuged (5,000×g, room temperature, 10 min) and the serum transferred to another labeled centrifuge tube. Glycerol was added to the serum for a final concentration of 10%. Most of the methods used fresh unfrozen serum. It was later found that serum that was stored frozen at −70° C. for extended times did not yield the same specific results as when the serum was fresh and unfrozen.

Polyacrylamide Gel Electrophoresis (PAGE)

For resolution of lower molecular weight components, 12% polyacrylamide gels (reagents from Sigma Chemical Co., St. Louis, Mo.) were prepared by the method of Laemnli (1970). For these, 1.88 ml of 40% acrylamide/1.3% BIS (N,N'methylene-bis-acrylamide), 1.45 ml 3 M TRIS (tris-hydroxymethyl-aminomethane), buffer, pH adjusted to 8.9 with hydrochloric acid, 0.5 ml 2% SDS (sodium dodecyl sulphate, do not use for native gels), 10 µl TEMED (N,N.N', N'-tetramethylethylenediamine), 100 µl 10% ammonium persulphate and 6.08 ml of triple-distilled water were combined. For separating components of higher molecular weight, a 7.5% polyacrylamide gel was used.

Electrophoresis was done in a BioRad™ minigel system following the protocols outlined by the manufacturer. The acrylamide was loaded into the glass chambers soon after preparation. About 10 ml was required for 2 mini-gels. As noted below, water-saturated butanol was added to the top of the liquid acrylamide to make an even surface. On top of the acrylamide was added the 4% "stacking gel". This was made with 0.5 ml of 40% acrylamide/1.3% BIS, 0.6 ml of 3 M TRIS (pH 8.9), 0.25 ml of 2% SDS (SDS is not used for native gels), 5 µl of TEMED, 50 µl of ammonium persulfate and 3.7 ml of triple-distilled water. The stacking gel was loaded onto the acrylamide layer soon after preparation.

For electrophoresis, a 10-fold strength electrolyte running buffer was made by combining 30 g of TRIS base, 144 g glycine and 10 g SDS (do not use for native gels) in 1 litre of triple distilled water. As only 500 ml of buffer was needed for each run, 50 ml of this and 450 ml of water was combined.

A double-strength buffer for samples consisted of 100 mM TRIS-HCl (pH 6.8) and 200 mM DTT (dithiothreitol) with 20% glycerol, 2% SDS (absent for native gels) and 0.1% bromophenol blue.

For the procedure, 4 glass walls and 3 spacers were placed in the apparatus holder. Eight mm from the top of the glass walls was measured (one could use the stacking comb as a place holder), and then a line was drawn on the glass. With a 1 ml pipette and pipetter, the acrylamide (12 or 7.5%) solution was added up to the marked line. Enough water-saturated butanol was added to provide a layer that evened the surface of the acrylamide. When the acrylamide solidified, the butanol was rinsed out with water, the water removed and the remaining excess water removed by blotting with filter paper. A comb (thick 14 well comb) was inserted between the glass walls and stacking gel was dispensed over the acrylamide. The stacking gel was allowed to set. The comb was then removed, the two gels were taken from the setting apparatus and these were placed in carriers to be placed in the mini-gel boat. For the bottom, the gel boat was filled with running buffer (single strength) to ⅓ the height of the gels. For the top, running buffer was added and any bubbles in the stacking gel spaces were removed with a Pasteur pipette. A small amount of sample buffer was placed in each well to identify the location for sample loading. Samples were diluted 1:1 with 2-fold strength sample buffer, boiled for 10 minutes, vortexed for 5 seconds, cooled, then centrifuged for 10 seconds at maximum speed in an Eppendorf™ desktop centrifuge (244,000 rpm). A total of 10 µl was transferred to each well in the gel. Samples were run at a constant voltage of 100 V until the dye front reached the end of the gel. Duplicate gels were run concurrently for a protein stain and an immunoblot.

Protein Staining of Polyacrylamide Gels

Polyacrylamide gels were stained in large Petri dishes (from Fisher Scientific, Edmonton) containing 0.025% Coomassie Brilliant Blue R250, 40% methanol, 7% acetic acid and about 53% water (this solution both fixed and stained the proteins). The gels were placed in this solution and the plate was rocked for a few hours. Destaining (removal of dye from the gel where proteins were not present) was done with several changes of 40% methanol, 7% acetic acid and 53% water. Once destained, the gels were stored in 5% glycerol in water.

Molecular weight standards (Bio-Rad Laboratories, Mississauga, Ontario), that were run as sample on the first and last wells, varied depending on the desired range for the test samples. Broad range standards included myosin (200 kDa), beta-galactosidase (116 kDa), phosphorylase B (97 kDa), bovine serum albumin (66 kDa), ovalbumin (45 kDa), carbonic anydrase (31 kDa), soybean trypsin inhibitor (22 kDa), lysozyme (14 kDa) and aprotinin (6.5 kDa). Low range standards ranged from phosphorylase B to lysozyme, high range standards ranged from myosin to ovalbumin.

Western Immunoblots

Following electrophoresis, the gel was electro-blotted onto a nitrocellulose membrane (Hybond, ECL Chemicals, Amersham Pharmacia Life Sciences, Baie Dorfe, Quebec) in a BioRad (Mississauga, Ontario) mini Protean-2-electrotransfer apparatus. The transfer buffer was 3 g of Trizmabase (Sigma Chemicals, St. Louis, USA), 14.4 g glycine and 200 ml of methanol with water to make 1 litre. To block binding sites on the nitrocellulose membrane where proteins were not present, the membrane was placed into an 8 cm Petri dish containing a 5% solution of blocking reagent (ECL blocking agent, ECL Chemicals, Amersham Pharmacia Life Sciences, Baie Dorfe, Quebec) and phosphate buffered saline with 0.1% Tween-20 (PBS-Tween). This preparation was then incubated for an hour at room temperature (22° C.) with gentle swirling on a flat-top rotational shaker (set at 60 rpm). The membrane was then washed for 10 minutes in PBS-Tween, followed by 3 subsequent washes of 5 minutes each. Serum (from control unvaccinated mice, mice infected with *B. abortus* 30, mice vaccinated then infected with 10 LD50 of *F. tularensis* LVS, or rabbit anti-*F. tularensis* antiserum) was the primary "detector" antibody diluted 1:1000 in PBS-Tween. The nitrocellulose membrane was incubated in 50 ml of this antibody solution for 1 hour in PBS-Tween as before. The second "indicator" antibody was a Caltag (Caltag Laboratories c/o Cedarlane Laboratories Ltd., Hornby, Ontario) anti-mouse (or anti-rabbit) antibody conjugated to horseradish peroxidase, diluted 1:30,000 in 50 ml of PBS-Tween and incubated at room temperature for an hour with gentle swirling. The membrane was then washed in PBS-Tween as noted above. Following the last wash, the membrane was placed onto a clean, dust-free sheet of acetate. A 5 ml volume of a 1:1 solution of A and B (ECL Chemicals, Amersham Pharmacia Life Sciences, Baie Dorfe, Quebec) was placed onto the membrane and this activated the antibody-HRP to fluoresce and emit light. This was left for 1 minute on the membrane and then the excess was wicked away with a paper towel. A second strip of acetate was layered on top of the membrane (care was taken to avoid entrapped bubbles). This "sandwich" was then transferred into an exposure cassette and taped in place. Sensitized X-ray film (ECL Hyperfilm, Amersham Pharmacia Life Sciences, Baie Dorfe, Quebec) was added to the cassette under safelight (red light) conditions. Fluorescent activated antibody-HRP was allowed to expose the film for 40 minutes. The film was then removed from the cassette and developed in Kodak GBX developer until it appeared dark by inspection under a safelight. The film was then fixed for 3 minutes and washed thoroughly in distilled water for another 5 minutes. It was dried overnight, photographed and stored.

Silver Stain (for Proteins and Lipopolysaccharide)

For proteins, the Bio-Rad™ (Mississauga, Ontario) silver stain was used (with dichromate as the oxidizer). For lipopolysaccharide (LPS), periodic acid was used to oxidize carbohydrates, such as those in the O-polysaccharide and core region of LPS, and to activate these for a reaction with silver. The procedure of Bio-Rad™ silver staining for proteins was followed except that periodic acid was used, instead of dichromate, as the oxidizer. The polyacrylamide gel was added to a Petri dish and then 50 ml of "fixer" (25% isopropanol, 7% acetic acid, 68 ml triple distilled water) was added, incubated at room temperature for 15 minutes, discarded, then fresh "fixer" was added and incubated for another 15 minutes. The "fixer" was discarded, a few ml of "oxidizer" (0.7% periodic acid, 40% ethanol, 5% acetic acid, 54.3% water) was used to rinse the plate, and then 50 ml of "oxidizer" was added and allowed to incubate for 5 minutes. The plate and gel were rinsed by adding 50 ml of distilled water and gently swirling this on a flat-top rotational shaker for 10 minutes. The water was discarded and then 50 ml of "silver reagent" (the Bio-Rad™ silver staining solution was diluted 1:10 in triple distilled water) was added and the plate incubated for 20 minutes. The gel was lightly rinsed for about 30 seconds with distilled water delivered by a squeeze bottle and then "developer" (1.6% Bio-Rad™ developer powder in water) was added (incubation was variable, anywhere from 1-15 minutes depending on the reaction intensity). Fifty ml of 5% acetic acid was then added as the stopping bath.

Protein Determination

To conserve on test samples while being able to assess a wide range of dilutions, a microtitre assay was done. Each assay was performed in a 96-well, flat bottom, sterile microtitre plate (Nalgene™). Eighty microlitres (80 µl) of triple-distilled water was added into wells 2 through 12 for all rows (A-H) to be used. Eighty microlitres of the bovine serum albumin standard was added to well A1. Eighty microlitres was also added to A2 (for 160 µl of a 1:2 dilution). Eighty microlitres from A2 was transferred to A3 and with unused pipette tips the standard was diluted across the row. Test samples were diluted in the same manner in the other rows. Eighty microlitres of the Bio-Rad™ Protein Assay Dye reagent concentrate (Bio-Rad Laboratories, Mississauga, Ontario) was added to each well, thoroughly mixed and then left to incubate for 5 minutes at room temperature. The plate was then read at 595 nm in a Thermomax™ microtitre plate reader (Molecular Devices, Sunnyvale, Calif.). The results were analyzed with the software program, Softmax™ (also by Molecular Devices) using the supplied 4-parameter fit.

Sample Preparations

For *Francisella tularensis* LVS cultures grown in broths, after 3 days of incubation the culture was centrifuged, then had the supernatant removed and filter-sterilized through a 0.22 µm Nalgene filter sterilizing flask (1 litre). Part of the supernatant volume was stored in the refrigerator, part was freeze-dried. The bacterial pellet was resuspended in PBS, frozen at −70° C. then thawed when required and sonicated as noted in the previous section.

For cultures grown on agar plates, after incubation for about a week, cells were scraped off the agar surface, the agar from a plate was cut into pieces, transferred to a plastic bag, 50 ml of sterile PBS was added, the bag sealed and then contents crushed on a Stomacher (Seward, UK) for 3 minutes. The bag was then opened, the slurry transferred to a centrifuge bottle, this was centrifuged (10,000×g, 4° C., 30 min), the supernatant removed then filter-sterilized as before. Part of this latter supernatant was stored in the refrigerator, part was freeze-dried.

Bacterial cell sonicates, with components released into PBS, were separated from unbroken cells or cell debris by centrifugation (10,000×g, 4° C., 30 min). The liquid (referred to as cell lysate) was placed into a Spectrapor 10,000 m.w. cutoff dialysis bag and dialyzed (overnight at 4° C.) against 1 mM HEPES and 1 mM DTT (dithiothreitol).

As required, the components of these various supernatant preparations were concentrated with an Amicon ultrafiltration membrane (Millipore, Nepean, Ontario) with a 30,000 m.w. cutoff. Once the membrane was fitted into the unit, and the preparations were added, the unit was sealed and dry nitrogen was used to pressurize the unit to 55 psi. The retentate, containing components larger than 30 kDa, was collected and stored at 4° C.

Nitric Oxide and Cell Viability Determination

The macrophage cell line J774.1 was grown on sterile Falcon™ 96-well tissue plates (Fisher Scientific, Edmonton) using mMEM without phenol red, supplemented with streptomycin (10 µg/mL), penicillin (10 U/ml), fungizone (0.25 ug/ml) and 5% horse serum. Initial concentration of macrophages was about 5000 cells/well. As a control and blank, the bottom row did not have cells. Volumes of 50 µl fresh medium and 50 µl serially diluted (done in triplicate) test sample were added to the wells. After 24 hrs, the media were transferred to a fresh microtitre plate and an equal volume of Griess reagent (1% sulphanilamide, 0.1% napthylethylene-diamine dihydrochloride, 2.5% $H_2PO_4$) was added for nitrate determination (Green et al., 1982). This mixture was incubated at room temperature for 10 minutes and then read at 540 nm in a microtitre plate reader (Molecular Devices, Sunnyvale, Calif.). Sodium nitrate was used as a standard for nitrate quantitation.

Concurrently, cell viability was assessed using Alamar-Blue™ (AccuMed International Inc., Westlake, Ohio). A tenth ml of a 10% (v/v) concentration was added to each well. The plate was incubated for 5 hours at 37° C., 90% humidity, 5% $CO_2$. The absorbence (570 nm) was read on a Thermomax™ titre plate reader (Molecular Devices, Sunnyvale, Calif.), the bottom row without cells served as the control and blank.

Column Chromatography Fractionation/Purification

Cell lysates (i.e. components released by sonication that went into PBS) and freeze-dried supernatants from *F. tularensis* LVS cultures were purified by column chromatography. A twin-pump Pharmacia FPLC™ unit (Amersham Pharmacia Life Sciences, Baie Dorfe, Quebec) was used which included a chart recorder coupled to a ultra-violet detector (214 nm) and a 50 ml loading loop. Two buffers were used. Buffer A comprised of 10 mM HEPES, Buffer B comprised of 10 mM HEPES and 3 M KCl. To elute bound components from the column, a gradient was programmed to raise the percentage of B-buffer to 50% over a time of 20 minutes, following the loading step. To increase binding, samples were dialyzed overnight in a Spectrapor 8 kDa molecular weight cut-off membrane against triple-distilled water (to remove salts and other small molecular weight components). The dialyzed material was loaded into the 50 ml loop and subsequently injected onto the column. The column used was a Pharmacia Mono-Q 10/10 column. Flow rate was set at 1.0 ml/minute and the chart speed was fixed at 5.0 mm/minute. The absorbance at full scale was set at 2.0 with a 10% offset. Fractions were collected in 1.0 minute intervals.

Results and Discussion (a) Initial Studies

In a previous publication, we reported that by subculturing the *F. tularensis* live vaccine strain in a synthetic salts medium (Chamberlain's medium) rather than complex peptone-cysteine medium, that its virulence for mice could be enhanced 1000-fold (Cherwonogrodzky et al., 1994). Our report of a greatly enlarged capsule under these former growth conditions "taught away" from subsequent observations of another virulence factor. As described in the previous section (see Detailed Description of the Invention), we had novel undisclosed observations that the virulence of *F. tularensis* LVS (grown in a synthetic medium) was more likely due to a factor other than the capsule. The reasoning for this was that it appeared that virulence of the bacterium was unrelated to the presence of capsule (virulence was lost in the third to fifth subculture while capsule formation was unchanged). It was also observed that filter sterilized culture supernatants (free of the bacterial cell) were lethal for mice but that their effect was delayed, causing death only after 1-2 days. Also, the presence of microscopic foci of necrosis and pneumonia in the lung in infected mice suggested host cell death occurred in susceptible lung tissue but not other tissues studied.

The initial work focused on protein profiles of freeze-dried components secreted by *F. tularensis* LVS grown in synthetic medium. The cultures examined were both agar (i.e. components extracted from the agar and into liquid PBS) and broths (i.e. the supernatant of broth cultures). Eighty mg of these freeze-dried samples were dissolved in a ml of distilled water and used on a 12% SDS-PAGE. The Coomassie stain for proteins was not sensitive enough to detect the low amount of proteins present in the samples. A more sensitive silver stain for proteins was used and indeed proteins were detected with this method.

Figure 1:
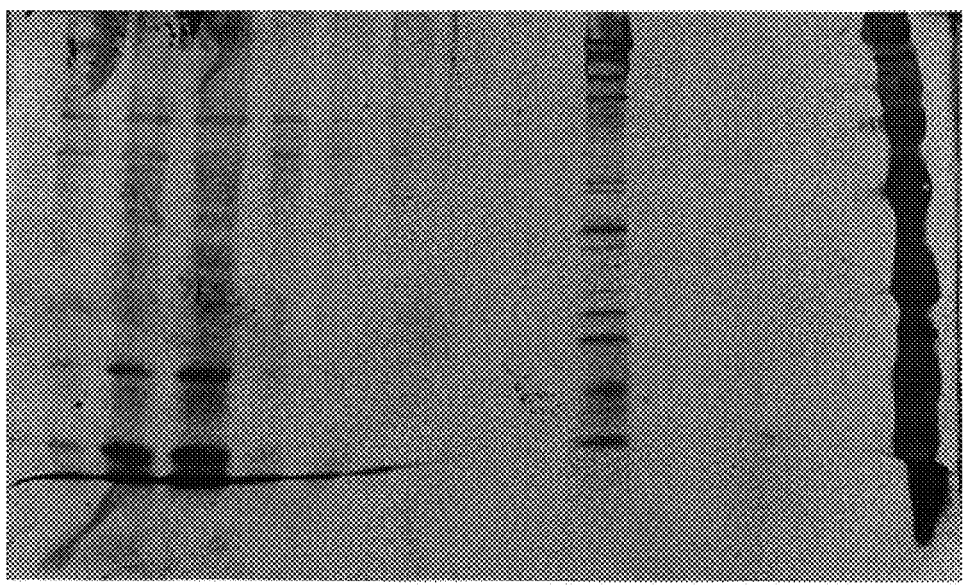
FIG. 1 shows a 12% SDS PAGE, Silver Stain, of *Francisella tularensis* live vaccine strain (LVS) sequentially subcultured on synthetic salts medium (Chamberlain's) and the supernatants of either agar (A1-A6) or broth (B1-B6) cultures inspected for proteins.

As we have noted previously in this patent, the pathogenicity of *F. tularensis* (LVS), subcultured in a synthetic salts medium, appeared to be transitory. Its ability to kill mice increased until about the third subculture and then diminished after this, even though capsules remained prevalent throughout these subcultures. FIG. 1 shows that this transition is also reflected in the silver stain of the supernatants. When the bacterium was subcultured on an agar synthetic salts medium, the protein profiles increased until the third subculture and then these diminished. For the bacterium subcultured in broth synthetic salts medium, only the third subculture showed that proteins were released into the supernatant. The profiles appeared to differ between proteins released when the bacterium was grown in agar medium and proteins released when it was grown in broth medium. It should be noted that as the bacteria were grown in a simple salts medium, lacking any proteins, all the proteins evident are due to the bacterium and not to any medium contaminants.

It is noted that, when one compares the protein profiles of bacterial proteins secreted into the medium of agar or broths, and the protein profiles of the cells disrupted by sonication to mimic lysis, these differed as shown in FIG. 2. Evidently specific proteins were being secreted under these conditions and the profile was not just a reflection of all the proteins in the cell that might be released if the cell had lysed.

We interpret the above as a sign of growth stress imposed on the bacterium. It was likely that, during subcultures 1-3, the bacterium was adapting to the restrictive synthetic salts medium. The stress of being grown in a sub-optimal medium may have caused the expression and release of components that are also expressed during the course of an infection when the bacterium is acquiring metabolites for growth. Subcultures 4-6 may reflect that the bacterium had adapted to the medium, did not require additional metabolites and suppressed the expression of these components.

This same transition of virulence and toxin expression when a bacterium is grown in synthetic salts medium has also been observed for *Vibrio parahaemolyticus* and its expression of the Kanagawa hemolysin (Cherwonogrodzky, thesis, 1983).

(b) Characterization of an *F. tularensis* LVS 52 kDa Protein

The above showed that proteins were present in the supernatants of the different preparation. The results also showed that these and other components were secreted, rather than released by lysis. To date it has been unobvious for an investigator in the field to assess proteins secreted into the medium from stressed cells grown in a synthetic salts medium. Instead, most of the studies deal with membrane proteins associated with the bacterial cell grown under optimal conditions.

We investigated the secreted proteins that we had in culture supernatants to verify whether they have any bearing on the disease process of tularemia.

A Coomassie Blue or a silver stain shows what proteins are present. It does not necessarily mean that these proteins secreted into the medium are significant in the disease process. To resolve this, the medium extracts or the broth supernatants were freeze-dried and then investigated with Western immunoblots (antigens are separated by electrophoresis, transferred to a membrane, and the antibodies in serum from affected animals are used as probes to identify antigens of importance in the disease process). Initially a commercial rabbit anti-tularemia antiserum was used. Results were negative (data not shown). The antibodies produced in rabbits that were vaccinated with killed *F. tularensis* cells (the SCHU strain grown in complex medium) did not recognize the antigens released into the medium that we have discovered with a live culture of *F. tularensis* LVS grown in a synthetic salts medium.

Next, antisera from mice that had been infected with *B. abortus* were used. As *B. abortus* and *F. tularensis* proteins and O-polysaccharide (OPS) cross-react (Van Hoek et al., manuscript in preparation, data unpublished as yet) it was thought that mouse anti-*Brucella* serum might serve as an antibody source to identify *F. tularensis* antigens. Results were again negative (data not shown, negative results on DRES file 98-08-04-b).

It was then undertaken to prepare antisera unobvious to one skilled in the art of tularemia. At our DRDC Suffield laboratory, we have developed an O-polysaccharide vaccine from *B. abortus* that protects mice from brucellosis. This vaccine also cross-protects mice from tularemia (results unpublished). We vaccinated mice with the OPS vaccine against *B. abortus* and then infected these animals with several lethal doses (10 $LD_{50}$) of *F. tularensis* LVS. In the past usually no unvaccinated control mice survived this dose. In contrast, usually 60% of vaccinated mice will survive this multiple lethal dose infection and indeed during this study 12 of 20 vaccinated mice survived. The antisera from mice that had survived the course of tularemia would likely have antibodies to antigens related to the disease process caused by the living bacterium. Upon doing immunoblots of cell lysates with this antisera (from mice that survived tularemia), antibodies did label components not evident with antisera from rabbits vaccinated with killed whole cells of F. tularensis nor mice infected with B. abortus. The predominant protein detected was estimated to have a molecular weight around 52 kDa (see FIG. 3).

When supernatant preparations that contained this 52 kDa protein were digested with proteinase K, it vanished, showing that it was indeed a protein (DRES file 00-03-13-a). Also, we observed that post-translational modifications did occur but that these were not consistent. On some occasions this protein appeared to be a doublet of 52 and also 53 kDa (DRES file 98-07-27-a). Usually the 52 kDa protein did not have carbohydrate as evidenced by a lack of reaction with periodate treatment followed by silver staining. On the occasions when it did show glycosylation (unfiled, photograph available) tentatively we can describe this as being similar to the O-polysaccharide of B. abortus because the anti-52 kDa antiserum also reacted with a component in cell lysates of Escherichia coli O:157H:7 and Pseudomonas maltophilia 555. The only component known to be common to B. abortus, F. tularensis and these latter two bacteria is the O-polysaccharide (data not shown, DRES photograph file number 00-04-17-a).

It was also observed that the immunoserum bound to the high molecular weight protein myosin that was in the molecular weight protein standards. We did not pursue whether this binding was due to cross-reaction between myosin and F. tularensis proteins, or whether as a consequence of active tularemia the mice had made auto-antibodies to their own myosin. In either case, anti-myosin antibodies might be a novel indirect test for identifying tularemia in an animal or human.

It was investigated whether this 52 kDa protein, initially found outside the cell grown in agar or broth synthetic salts medium, could also be found inside the cell when the above mentioned immunoserum was used. Usually the third broth subculture yielded the greatest amount of 52 kDa protein in the supernatant. Francisella tularensis was subcultured twice in broth, and then 1 ml was transferred to eight 500 ml flasks containing 100 ml of synthetic salts medium. Every day afterwards, a flask was removed, the culture was centrifuged (10,000×g, 30 minutes, 4 C), the supernatant discarded, the cells resuspended in 10 ml of saline, the cells were disrupted by sonication, and then the preparations were standardized by diluting to 3 mg/ml. FIG. 4 shows that the 52 kDa protein is also found within the cell, although it appears to increase until the culture reaches stationary phase (i.e. day 5, note that it appears as a doublet). Afterwards it appears to persist though it does appear to decrease in amounts as the culture matures (i.e. until day 8).

(c) Identification of the 52 kDa Protein as a Toxic Virulence Factor

Other researchers have studied the proteins of F. tularensis LVS, but their investigations led to the study of low molecular weight proteins, specifically a 17 kDa protein (Sjostedt, 1997) that did not appear to be a virulence factor. In our study, a striking result of immunostaining with the use of antiserum, taken from vaccinated mice that survived multiple lethal doses of F. tularensis LVS, was the identification of a prominent F. tularensis 52,000 molecular weight (52 kDa) protein. Obviously it played some role in the disease process. We verified whether this 52 kDa protein was, in fact, a toxic virulence factor of F. tularensis.

The 52 kDa protein was purified by taking the supernatant of the third subculture of F. tularensis LVS grown in the synthetic salts medium (removing the cells by centrifugation), filter sterilizing this through a 0.45 µm filter, fractionating and concentrating the solution by using an Amicon™ filtration with 30,000 m.w. cutoff (i.e. proteins greater than 30 kDa were retained). This concentrate was then fractioned on a Pharmacia Mono-Q™ column (which separates proteins on the basis of charge and hence isoelectric points, see FIG. 5). Proteins were eluted with increasing concentrations of potassium chloride. Dialysis against saline removed this potassium chloride. Although Fraction 24 had the greatest amount of the 52 kDa protein (as shown by the samples being electrophoresed on SDS-PAGE gels, followed by Coomassie blue™ staining), Fraction 29 was used in further studies because despite being more dilute, contaminating proteins were less evident.

When HELA (human, cancer) cell cultures were first tested for sensitivity to this 52 kDa protein, no effect was observed. However, when Vero (Green Monkey Kidney Cells) cell cultures were used, cell death was observed, especially if the preparation of the 52 kDa protein was concentrated by freeze-drying and then dissolved in a minimal amount of sterile saline. The 52 kDa protein also affected cell cultures of J774A.1 cells (derived from balb/c mouse macrophages). The test sample was standardized by the amount of protein given. When the amount of protein was greater than 0.5 mg/ml, cell death for both tissue cultures did occur (about 50% death at 1 mg/ml)(FIG. 6) but only after 24 hr incubation. These results support the preliminary observations made a decade previously that F. tularensis produces a component that is toxic but that its effects are not immediate and it affects only susceptible tissues. For protein amounts less than 0.1 mg/ml, cell death was not observed.

When mammalian cells are stressed, these may produce nitrous oxide. For J774A.1 mouse macrophage cells, nitrous oxide production correlated with the amount of the 52 kDa protein in the different Pharmacia Mono-Q™ fractions noted above (FIG. 7). Nitrous oxide also increased when protein amounts went from the sublethal amounts of 0.1 mg/ml to 0.5 mg/ml (FIG. 8). For higher amounts, the cells had been killed and hence did not express nitrous oxide. With the 52 kDa protein stressing the mammalian cells to produce nitrous oxide, or this protein killing the cells at higher concentrations, our results strongly suggest that the 52 kDa protein was a toxin. The observation a decade ago of delayed death for mice given 0.050 ml of culture supernatant intranasally can now be described as initiation of host cell stress and a cascade of negative metabolic responses.

(d) Vaccine/Immunization Studies

Experiments were conducted to determine whether this 52 kDa protein was a potential vaccine candidate.

As time restraints allowed only a brief inspection of vaccine potential, a rapid screen was done. Two hundred and fifty (250), rather than 10, $LD_{50}$s of F. tularensis LVS were given to eliminate components of only marginal vaccine efficacy. The infection was given intranasally, rather than intraperitoneal, to reflect a biological warfare scenario of challenge. Outbred CD1 mice, rather than inbred balb/c mice, were used to reflect genetic diversity more relevant to human populations. Mice were monitored for 3 weeks rather than 1 week to account for any delayed responses and to ensure that recovery was complete. Table 1 shows that some of these vaccine, or vaccine combinations, gave obvious protection even under these exceptionally harsh challenges.

TABLE 1

Assessment of different vaccine candidates for the protection of CD1 mice against 250 $LD_{50}$s of F. tularensis LVS given intranasally.

| GROUP | VACCINATION (given i.p.) | PROTECTION FROM CHALLENGE (from 250 $LD_{50}$ F. tularensis LVS) |
|---|---|---|
| 1 | Control (no vaccination, only 0.1 ml sterile PBS/mouse given) Different Brucella vaccine formulations: | 0/5 mice (0%) |
| 2 | B. abortus 1119-3 O-polysaccharide (OPS) (1 µg/mouse) | 2/5 mice (40%) |
| 3 | B. melitensis 16 M OPS (1 µg/mouse) | 0/5 mice (0%) |
| 4 | B. suis 145 OPS (1 µg/mouse) F. tularensis cell lysate | 0/5 mice (0%) |
| 5 | F. tularensis cell lysate (2 µg/mouse) F. tularensis broth culture supernatant, fractioned by Amicon | 5/5 mice (100%) |
| 6 | >(Greater than) 30 kDa (2 µg/mouse) | 1/5 mice (20%) |
| 7 | >30 kDa (2 µg/mouse) + B. suis OPS vaccine (1 µg/mouse) Purified 52 kDa component (Fraction #29) | 5/5 mice (100%) |
| 8 | Fraction #29 (2 µg/mouse) | 1/5 mice (20%) |
| 9 | Fraction #29 (2 µg/mouse) + B. suis OPS vaccine (1 µg/mouse) | 2/5 mice (40%) |

From the above, all control mice (Table 1, Group 1) died from this high dose of F. tularensis LVS as expected.

Different species of Brucella will express different forms of the polysaccharide on the cell wall. When different Brucella O-polysaccharide vaccines were tested, B. abortus OPS (Group 2) appeared to give the best protection against tularemia in mice. It is likely that the other polysaccharides are also protective, but only against a lower lethal dose than that used in our screening experiments. We have found that the polysaccharide of Brucella abortus cross-reacts with the polysaccharide of F. tularensis LVS (unpublished data). The significance of these sugars, and glycosylation of proteins, will be discussed below.

In the past, vaccination with whole killed F. tularensis cells have not given immunity for mice. This teaches away from our own results where we used F. tularensis cells, stressed in a synthetic salts medium to express the 52 kDa protein, then lysed by sonication to release this component (unbroken cells and cellular debris were removed by centrifugation). Using this noted lysate gave remarkable total protection for the mice from tularemia (Group 5).

The entire bacterial lysate may be unnecessary to protect mice from tularemia. A fraction of proteins greater than 30,000 molecular weight was prepared with the use of the Amicon™ filtration unit. Although some protection was noticed for this fraction (Group 6), remarkable total protection occurred when bacterial polysaccharide was included (Group 7).

As our studies have shown that the 52 kDa protein was identified as a significant factor in the disease process of tularemia (i.e. by antibodies in "survivor" serum), we vaccinated mice with this component (Group 8). It did protect to a minor extent and this protection was enhanced with B. suis OPS vaccine (Group 9). In hindsight, we should have vaccinated the mice with polysaccharide from either B. abortus or from F. tularensis LVS to enhance the efficacy of the 52 kDa protein.

As noted previously, for immunoblots with lysates of Escherichia coli O:157,H:7, Salmonella godesberg, and Pseudomonas maltophilia 555, antibodies (from the serum from vaccinated mice that survived tularemia) strongly bound to some of the proteins. As these bacteria share cross-reactive polysaccharides, the results suggest that cross-protection was due in part to cross-reaction to the carbohydrates. As noted previously in this patent, we did find that the 52 kDa protein was glycosylated in some cultures of F. tularensis LVS. We believe that this glycosylation enhances the entry of this toxin into its target cells. One can either protect a mammal from the effects of the toxin by vaccinating with the toxin (Group 8) and by logical extension a toxoid, with the glycosylating component or a polysaccharide similar to this component (Group 2) or with both the toxin and the polysaccharide which act synergistically to enhance protection (Group 7 and Group 9).

(e) Additional Studies

Time allowed us only to pursue the 52 kDa protein, which appeared to be the most striking of proteins secreted or released by F. tularensis LVS stressed in a synthetic salts medium. However, there were other proteins of note (see FIG. 9). When the preparation was digested with proteinase K, these proteins were digested and did not appear in polyacrylamide gels (Lane 3). Digestion with lipase caused the loss of a 45 kDa lipoprotein (lane 5). Digestion with DNAse caused the shift of a 19 kDa nucleoprotein to a higher 33 kDa protein, suggesting dimerization (Lane 7). Aside from identification by these preliminary characterizations, time did not allow us to assess their vaccine potential or whether these could act synergistically with the 52 kDa protein.

In the model of diphtheria toxin, bacteriophage influence the expression of toxins in Corynebacterium diphtheriae. We investigated if F. tularensis LVS harboured a bacteriophage that, although usually repressed and lysogenic with the bacterial chromosome, under the stressful condition of the bacterium being cultured in a synthetic medium, emerged to lyse the bacterium and hence release cell associated components such as the 52 kDa protein. We attempted to isolate phage, plasmids and extra-chromosomal material from culture cells and supernatants but were not successful.

It is to be understood that the embodiments and variations shown and described herein are merely illustrative of the principles of this invention and that various modifications may be implemented by those skilled in the art without departing from the scope and spirit of the invention.

What is claimed is:

1. An isolated subcellular protein having a molecular weight of about 52 kDa, said protein having been expressed from a *Francisella tularensis* subculture growing in synthetic salts medium at pH 6.5.

2. The subcellular protein of claim 1, wherein said protein is identified by immunological reaction with an antiserum or antibodies from said antiserum, said antiserum having been obtained from an animal which has been first vaccinated with O-polvsaccharide extracted from a *B. abortus*, which is immunologically cross-reactive with *Francisella tularensis*, and then survived challenge with a dose of the *Francisella tularensis* which would be lethal in the absence of said first vaccination.

* * * * *